US012611647B2

(12) United States Patent
Perez-Pellitero et al.

(10) Patent No.: US 12,611,647 B2
(45) Date of Patent: Apr. 28, 2026

(54) ZEOLITIC ADSORBENT FOR THE SEPARATION OF HYDROCARBON ISOMERS

(71) Applicants: IFP Energies Nouvelles, Rueil-Malmaison (FR); Arkema France, Colombes (FR)

(72) Inventors: Javier Perez-Pellitero, Rueil-Malmaison (FR); Ludivine Bouvier, Lacq (FR); Maria Manko, Rueil-Malmaison (FR); Maxime Moreaud, Rueil-Malmaison (FR)

(73) Assignees: IFP Energies Nouvelles, Rueil-Malmaison (FR); Arkema France, La Défense Puteaux (FR)

( * ) Notice: Subject to any disclaimer, the term of this patent is extended or adjusted under 35 U.S.C. 154(b) by 965 days.

(21) Appl. No.: 17/784,872

(22) PCT Filed: Dec. 18, 2020

(86) PCT No.: PCT/FR2020/052530
§ 371 (c)(1),
(2) Date: Dec. 2, 2022

(87) PCT Pub. No.: WO2021/123662
PCT Pub. Date: Jun. 24, 2021

(65) Prior Publication Data
US 2023/0219059 A1     Jul. 13, 2023

(30) Foreign Application Priority Data
Dec. 20, 2019     (FR) ....................................... 1915341

(51) Int. Cl.
| | |
|---|---|
| *B01J 20/18* | (2006.01) |
| *B01J 20/28* | (2006.01) |
| *C07C 7/11* | (2006.01) |
| *C07C 15/08* | (2006.01) |

(52) U.S. Cl.
CPC ......... *B01J 20/18* (2013.01); *B01J 20/28011* (2013.01); *C07C 7/11* (2013.01); *C07C 15/08* (2013.01)

(58) Field of Classification Search
None
See application file for complete search history.

(56) References Cited

U.S. PATENT DOCUMENTS

| | | |
|---|---|---|
| 2,985,589 A | 5/1961 | Broughton et al. |
| 3,558,730 A | 1/1971 | Neuzil |
| 3,558,732 A | 1/1971 | Neuzil |
| 3,626,020 A | 12/1971 | Neuzil |
| 3,663,638 A | 5/1972 | Neuzil |
| 3,878,127 A | 4/1975 | Rosback |
| 3,960,774 A | 6/1976 | Rosback |
| 6,136,198 A | 10/2000 | Adam et al. |
| 7,208,651 B2 | 4/2007 | Frey |
| 7,812,208 B2 | 10/2010 | Cheng et al. |
| 8,530,367 B2 | 9/2013 | Bouvier et al. |
| 9,061,918 B2 | 6/2015 | Bouvier et al. |
| 9,533,280 B2 | 1/2017 | Ackley et al. |
| 10,722,862 B2 | 7/2020 | Bouvier et al. |
| 10,940,458 B2 | 3/2021 | Laroche et al. |
| 2007/0224113 A1 | 9/2007 | Willis et al. |
| 2009/0326308 A1 | 12/2009 | Kulprathipanja et al. |
| 2013/0006031 A1* | 1/2013 | Leflaive ............ B01D 15/1821 585/821 |
| 2016/0009614 A1 | 1/2016 | Laroche et al. |
| 2016/0207025 A1 | 7/2016 | Laroche et al. |
| 2017/0217858 A1 | 8/2017 | Laroche et al. |
| 2017/0304799 A1* | 10/2017 | Bouvier ............ B01J 20/28071 |
| 2019/0160450 A1* | 5/2019 | Laroche ............ B01D 15/1821 |

FOREIGN PATENT DOCUMENTS

| | | |
|---|---|---|
| CN | 1191118 C | 3/2005 |
| CN | 104379250 A | 2/2015 |
| CN | 109562351 A | 4/2019 |
| DE | 102018109701 A1 | 10/2019 |
| JP | 2000-229238 A | 8/2000 |
| JP | 2014-193454 A | 10/2014 |
| JP | 2016-508065 A | 3/2016 |
| JP | 2016-515095 A | 5/2016 |
| JP | 2017-530854 A | 10/2017 |
| JP | 2019-519369 A | 7/2019 |
| WO | 2008009845 A1 | 1/2008 |
| WO | 2009081022 A2 | 7/2009 |

(Continued)

OTHER PUBLICATIONS

WO2018002174= English translation (Year: 2018).*
Office Action (The First Office Action) issued Feb. 28, 2024, by the National Intellectual Property Administration, P. R. China in corresponding Chinese Patent Application No. 202080088636.X and an English translation of the Office Action. (25 pages).
Breck, D., "Zeolites Molecular Sieves", John Wiley & Sons, 1973, 4 pages.
French Search Report for French Application No. 1915341, dated Dec. 20, 2019, 10 pages.
International Search Report and Written Opinion for International Application No. PCT/FR2020/052530, dated Mar. 30, 2021, 10 pages.

(Continued)

*Primary Examiner* — Stefanie J Cohen
(74) *Attorney, Agent, or Firm* — Buchanan Ingersoll & Rooney PC

(57) ABSTRACT

The present invention concerns a zeolitic adsorbent agglomerate comprising at least one zeolite of faujasite type comprising barium and/or potassium, of porosity between 25% and 45%, and having a standard deviation σ of crystal size distribution in said agglomerate of less than 0.30 μm.

The invention also concerns the use of the zeolitic adsorbent agglomerate for the separation of hydrocarbon mixtures, and the process for separating hydrocarbon mixtures using said zeolitic adsorbent agglomerate.

18 Claims, No Drawings

(56) References Cited

FOREIGN PATENT DOCUMENTS

| | | | |
|---|---|---|---|
| WO | 2014090771 | A1 | 6/2014 |
| WO | 2015/032923 | A1 | 3/2015 |
| WO | 2018002174 | A1 | 1/2018 |

OTHER PUBLICATIONS

Office Action (Examination Report) issued Apr. 24, 2025, by the Patent Office, Government of India, in corresponding Indian Patent Application No. 202217032816 with an English Translation of the Office Action. (6 pages).

Gomes et al., "Simulated Moving Bed Technology: Old and New", Adsorption, 2006, vol. 12, pp. 375-392.

Udemann-Hombourger et al, "The "VARICOL" Process: A New Multicolumn Continuous Chromatographic Process", Separation Science and Technology, 2000, vol. 35, No. 12, pp. 1829-1862.

Toumi et al., "Optimization of Simulated Moving Bed and Varicol Processes", Journal of Chromatography A, 2003, vol. 1006, pp. 15-31.

Office Action (Notice of Reasons for Rejection) issued Oct. 29, 2024, by the Japan Patent Office in corresponding Japanese Patent Application No. 2022-538368 and an English translation of the Office Action. (10 pages).

* cited by examiner

ZEOLITIC ADSORBENT FOR THE SEPARATION OF HYDROCARBON ISOMERS

CROSS-REFERENCE TO RELATED APPLICATIONS

This application is a 371 filing of International Application No. PCT/FR2020/052530, filed Dec. 18, 2020, which claims priority to French Application No. 1915341, filed Dec. 20, 2019, the disclosure of these applications being incorporated herein by reference in their entireties for all purposes.

FIELD OF THE INVENTION

The invention concerns the field of zeolitic adsorbents in the form of agglomerates comprising zeolite of faujasite type, for the separation of gaseous or liquid mixtures of aromatic hydrocarbons, and more particularly concerns processes for separating xylenes and in particular processes for separating para-xylene with improved productivity.

The present invention further concerns a process for separating gaseous or liquid mixtures of isomers with improved productivity, and more particularly a process for separating isomers of xylene with improved productivity for the production of highly pure para-xylene from a feed of aromatic hydrocarbons containing isomers having 8 carbon atoms.

BACKGROUND OF THE INVENTION

The use of zeolitic adsorbents composed of Faujasite zeolites (FAU) of type X or Y which, in addition to sodium cations, comprise barium, potassium or strontium ions, alone or in mixtures, for the selective adsorption of para-xylene in a mixture of aromatic hydrocarbons is well known in the prior art.

U.S. Pat. Nos. 3,558,730, 3,558,732, 3,626,020 and 3,663,638 show that zeolitic adsorbents comprising aluminosilicates containing sodium and barium (U.S. Pat. No. 3,960,774) or containing sodium, barium and potassium are efficient for the separation of para-xylene present in C8 aromatic fractions (fractions comprising aromatic hydrocarbons having 8 carbon atoms).

The adsorbents described in patent U.S. Pat. No. 3,878, 127 are used as adsorption agents in liquid phase processes, preferably of simulated counter-current type similar to those described in patent U.S. Pat. No. 2,985,589 and which inter alia apply to C8 aromatic fractions.

It is the objective of the invention to improve the productivity of existing processes for preparing para-xylene and in particular liquid phase processes, preferably of simulated counter-current type for separating isomers of xylene from C8 aromatic feeds. It has been surprisingly observed that this productivity can be improved through a judicious choice of the characteristics of the zeolitic adsorbent agglomerates used in processes of this type.

Separation in a simulated moving bed is to be construed herein in its broad meaning i.e. it may either concern a simulated counter-current moving bed or a simulated co-current moving bed, or it may relate to a so-called "Varicol" process. The Varicol process proposed by Ludemann-Hombourger (O. Ludemann-Hombourger, R. Nicoud, 2000) and later developed by Novasep, allows non-synchronized shifting of the inlet and outlet lines (Bailly, et al. 2004). The lengths of the four zones can be adjusted during a cycle by limiting the number of beds required to carry out separation.

The characteristic common to this family of processes is that the zeolitic adsorbent agglomerate (or more simply «solid adsorbent») is placed in a fixed bed, and the liquid streams in contact with the solid adsorbent are managed either by means of a set of «on-off» valves, or by means of a single complex valve known as a "rotary valve".

When the active element of the solid adsorbents used as adsorption agents in these processes is a zeolite, the latter obtained in crystal form is preferably used on industrial scale in the form of agglomerates. These zeolitic adsorbents agglomerated in the form of laminates, beads or extrudates, are generally composed of zeolite crystals, forming the active element with regard to adsorption, and of a binder intended to ensure the cohesion of the crystals in the form of agglomerates. This binder also imparts sufficient mechanical strength to the agglomerates to withstand the mechanical stresses to which they are subjected when used in operating units. These mechanical stresses are the cause of the formation of «fines», which lead to deteriorated performance throughout the operating time of the process.

The process for separating xylenes in a simulated moving bed (SMB) has undergone numerous technological improvements, in particular with respect to the liquid distributor plates, but relatively little progress concerning the intrinsic characteristics of the solid adsorbent.

Adsorbents for the separation of xylenes having improved transfer properties for the separation of xylenes are described for example in international application WO2008009845 which describes zeolite X adsorbents having small crystals of size smaller than 1.7 μm, of Si/Al atomic ratio such that $1.15<Si/Al≤1.5$, exchanged with barium, and optionally with potassium in international application WO2014090771 which describes agglomerated zeolitic adsorbents having optimized properties in particular for the separation of para-xylene from C8 aromatic fractions. These adsorbents exhibit maximum properties for para-xylene selectivity and mass transfer whilst having maximum mechanical strength associated with optimized adsorption capacity.

International application WO2018002174 proposes zeolitic adsorbents in the form of agglomerates having optimized properties for separating gaseous or liquid mixtures of isomers and more particularly for the separation of xylenes in gas or liquid phase and in particular of para-xylene from C8 aromatic fractions. The zeolitic adsorbents of the invention in particular display maximum properties for para-xylene selectivity and mass transfer whilst having improved strength and high adsorbent capacity per volume of adsorbent, and are particularly suitable for use in a separation process of para-xylene in liquid phase, preferably of simulated counter-current type.

In particular, this application teaches that a strong increase in macroporosity and/or mesoporosity is not desirable, hence in particle porosity, since this porosity does not take part in adsorption capacity. Optimization of diffusing properties and adsorption capacities were obtained by specifically selecting both porosity and tortuosity factor.

Patent application US2009/0326308 describes a separation process using an adsorbent with low binder content and containing type X faujasite crystals of nanometric size, typically a mean size of less than 500 nm.

In a process for separating xylenes via adsorption in a simulated moving bed, the zeolitic adsorbent is contacted with the liquid feed stream (feed mixture) most often comprising mixtures of C8 hydrocarbons, and generally and most often mixtures of xylene isomers and more particularly mixtures of ortho-xylene, meta-xylene, para-xylene and ethylbenzene.

By using a zeolitic adsorbent containing zeolite of faujasite structure having a Si/Al ratio between 1.0 and 1.5 (zeolites LSX, MSX, X) exchanged with barium or exchanged in majority with barium and in minority with potassium, para-xylene is adsorbed in the micropores of the zeolite in preference to all the other hydrocarbon compounds in the feed stream. The adsorbed phase in the zeolite micropores becomes enriched with para-xylene compared with the initial mixture forming the feed stream. On the contrary, the liquid phase becomes enriched with compounds such as ortho-xylene, meta-xylene and ethylbenzene in greater relative proportion than that characterizing the initial mixture forming the feed stream.

The liquid phase is drawn off from contact with the adsorbent thereby forming a stream of raffinate. The adsorbed phase enriched with para-xylene, is desorbed under the action of a flow of desorbent and drawn off from contact with the adsorbent thereby forming a stream of extract.

In the separation process of xylenes via adsorption in a simulated moving bed, the solid zeolitic adsorbent passes through one or two multi-stage columns to be contacted with the flow of liquid. A multi-stage column is a column composed of a multiplicity of plates arranged along a substantially vertical axis, each plate supporting a bed of particulate solid, and the different successive beds receiving the throughflow in series of the liquid or liquids used in the column. Between two successive beds there is a liquid distribution device feeding each bed of particulate solid.

In general, the operation of a column in a simulated moving bed can be described as follows:

A column comprises at least four zones and optionally five or six, each of these zones being composed of a certain number of successive beds, and each zone being defined by its position between an inlet line and an outlet line. Typically, a simulated counter-current unit (SCC) for the production of para-xylene is fed with at least one feed F to be fractionated (feed mixtures of aromatic hydrocarbons composed of isomers having 8 carbon atoms) and a desorbent D sometimes called eluent (generally para-diethylbenzene or toluene), and from said unit at least one raffinate R is withdrawn containing the feed products that are least selectively adsorbed and desorbent, and an extract E containing the product of the feed that is the most adsorbed and desorbent.

Other inlet and outlet lines can be added for rinsing the distribution circuits as described for example in patent U.S. Pat. No. 7,208,651. Since the addition of these additional rinsing flows in no way changes the operating principle of the SCC unit, for the sake of brevity we will not include these additional inlet and outlet lines in the description of the process of the invention.

The inlet and outlet lines are modified over time, shifted in the same direction by a value corresponding to one bed. Shifting of the different inlet or outlet lines can be simultaneous or non-simultaneous as taught in patent U.S. Pat. No. 6,136,198. The process according to this second operating mode is called Varicol.

Conventionally, 4 different chromatographic zones are defined in a column operating in simulated counter-current (SCC).

Zone 1: desorption zone of the most adsorbed product in the feed, positioned between injection of the desorbent D and withdrawal of the extract E.

Zone 2: desorption zone of the least selectively adsorbed products in the feed, positioned between withdrawal of the extract E and injection of the feed F to be fractionated.

Zone 3: adsorption zone of the most adsorbed product in the feed, positioned between injection of the feed and withdrawal of the raffinate R.

Zone 4: zone positioned between withdrawal of the raffinate R and injection of the desorbent D.

To increase the productivity of the separation process, the prior art teaches that one manner is to improve overall transfer into the zeolitic adsorbent agglomerate, and in particular by reducing the size of the crystals and/or the mean size of said agglomerates.

The prior art documents disclosing processes for pharmaceutical separation (Gomes et al., (2006), *Adsorption*, vol. 12, p. 375 sqq.) describe liquid phase chromatographic separation processes using agglomerates of size ranging from a few tens of micrometres up to 100 μm.

In these processes using adsorbents of very small size, the pressure drop $\Delta P$ is very high. For xylene separation processes, such levels of pressure drop $\Delta P$ are not frequent. It is nevertheless surprisingly observed that pressure drop $\Delta P$ is not a dimensioning criterion. It has particular impact on the thickness of the adsorber walls and on the power of operating units.

A further characteristic of the zeolitic adsorbent agglomerate is the rate of hydration of said agglomerate. Maintaining hydration of the zeolite at the desired value, for example loss on ignition of 4% to 7.7% for zeolite X, MSX or LSX, when used in a xylene separation process by adsorption in a simulated moving bed, is ensured by adding water to the feed and/or desorbent streams. The amount of water to be added for such levels of loss on ignition is such that the weight content of water in the hydrocarbon effluents (extract or raffinate streams) is most often between 0 ppm and 150 ppm, and more generally between 40 ppm and 150 ppm, when the adsorbent contains zeolite X, MSX or LSX.

Nevertheless, it is generally always necessary to increase the productivity of the process.

A first object of the present invention is therefore to propose a zeolitic adsorbent in the form of agglomerates having optimized properties for the separation of gaseous or liquid mixtures of isomers and more particularly for the separation of xylenes, in gas phase or liquid phase, in particular for the separation of para-xylene from C8 aromatic fractions. The zeolitic adsorbent agglomerates of the invention particularly display maximum properties of para-xylene selectivity and mass transfer, whilst having high mechanical strength and adsorption capacity, and are particularly suitable for use in a liquid phase separation process of para-xylene, preferably of simulated counter-current type.

For this purpose, the invention proposes an agglomerated adsorbent, preferably of faujasite zeolite having a Si/A atomic ratio of between 1.00 and 1.50, the particle porosity of which is advantageously between 25% and 45%, allowing the production of para-xylene of high purity with improved productivity, whilst avoiding degradation of performance over time. More specifically, the invention concerns a zeolitic agglomerated adsorbent comprising at least one faujasite zeolite of Si/Al atomic ratio between 1.00 and 1.50 limits included (FAU-X) and preferably comprising barium and optionally potassium, wherein first the particle porosity is between 25% and 45%, preferably between 30% and 45%, more preferably between 32% and 45%, further preferably between 35% and 45%, particularly advantageously between 36% and 45%, limits included, and secondly the standard deviation σ of crystal size distribution in said agglomerate is less than 0.30 μm, preferably between 0.05 μm and 0.30 μm, more preferably between 0.05 μm and 0.28 μm, further preferably between 0.1 μm and 0.28 μm, and most preferably between 0.1 μm and 0.25 μm, limits included.

SUMMARY OF THE INVENTION

Therefore, in a first aspect, the invention concerns an agglomerated zeolitic adsorbent comprising at least one faujasite zeolite of Si/Al atomic ratio between 1.00 and 1.50 limits included (FAU-X) and comprising barium and optionally potassium, characterized first in that the particle porosity of said adsorbent is between 25% and 45%, preferably between 30% and 45%, more preferably between 32% and 45%, further preferably between 35% et 45%, and particularly advantageously between 36% and 45% limits included, and secondly in that the standard deviation σ of crystal size distribution in said agglomerate is less than 0.30 μm, preferably between 0.05 μm and 0.30 μm, more preferably between 0.05 μm and 0.28 μm, further preferably between 0.1 μm and 0.28 μm, and most preferably between 0.1 μm and 0.25 μm, limits included.

In one embodiment, the agglomerated zeolitic adsorbent of the invention comprises zeolite crystals of number-weighted mean diameter less than 1200 nm, preferably between 100 nm and 1200 nm, more preferably between 400 nm and 1200 nm, further preferably between 500 nm and 1200 nm, still further preferably between 550 nm and 1200 nm, and most advantageously between 600 nm and 1200 nm, limits included.

In another embodiment, the agglomerated zeolitic adsorbent of the invention is in the form of beads of mean diameter between 100 μm and 1000 μm, preferably between 100 μm and 600 μm, more preferably between 200 μm and 550 μm, limits included.

In one preferred embodiment, said at least one FAU-X zeolite of the agglomerated zeolitic adsorbent of the invention has a Si/Al atomic ratio of between 1.05 and 1.50, preferably between 1.05 and 1.40 limits included, more preferably between 1.10 and 1.40 limits included.

In another preferred embodiment of the invention, no zeolitic structure other than the faujasite structure, preferably no zeolitic structure other than the faujasite X structure is detected by X-ray diffraction in the agglomerated zeolitic adsorbent of the invention.

In addition, it is preferred that the weight fraction of FAU zeolite, and preferably the weight fraction of FAU-X, zeolite, is higher than or equal to 80% relative to the total weight of the agglomerated zeolitic adsorbent of the invention.

The agglomerated zeolitic adsorbent of the invention comprises one or more alkali or alkaline-earth ions, preferably selected from among sodium, barium and potassium.

In one preferred embodiment, the content of barium, expressed in barium oxide (BaO) in the agglomerated zeolitic adsorbent of the invention is higher than 10%, more preferably higher than 15%, further preferably higher than 20%, still further preferably higher than 23%, even higher than 33% by weight relative to the total weight of the adsorbent, and advantageously said barium content is between 23% and 42%, and typically between 30% and 40% by weight, limits included, relative to the total weight of the adsorbent.

In another preferred embodiment, the content of potassium, expressed in potassium oxide ($K_2O$) in the agglomerated zeolitic adsorbent of the invention is lower than 25%, preferably between 0 and 20%, more preferably between 0 and 15% by weight, limits included, relative to the total weight of the adsorbent.

In one embodiment of the present invention, the loss on ignition of the agglomerated zeolitic adsorbent of the invention, measured at 900° C. according to standard NF EN 196-2, is lower than or equal to 7.7%, preferably between 0 and 7.7%, more preferably between 3.0% and 7.7%, further preferably between 3.5% and 6.5% and advantageously between 4.5% and 6%, limits included.

In another aspect, the present invention concerns the use of the agglomerated zeolitic adsorbent such as just described, in processes:

to separate C8 aromatic isomer fractions and xylenes in
        particular, and more particularly para-xylene;
    to separate isomers of substituted toluene such as nitro-
        toluene, diethyltoluene, toluenediamine, and others;
    to separate cresols;
    to separate polyhydric alcohols.

Finally, in a further aspect, the present invention concerns the process for separating para-xylene from aromatic isomer fractions having 8 carbon atoms, using as para-xylene adsorbing agent an agglomerated zeolitic adsorbent such as previously defined and more specifically in the remainder hereof.

The process for separating para-xylene from isomer fractions of aromatic hydrocarbons having 8 carbon atoms, according to the present invention, is conducted in gas phase or liquid phase, preferably in liquid phase via adsorption of para-xylene in the presence of a desorbent, said desorbent preferably being selected from among toluene and para-diethylbenzene.

In one preferred embodiment, the process for separating para-xylene according to the present invention is a process of simulated moving bed type, more preferably of simulated counter-current type.

DETAILED DESCRIPTION OF THE INVENTION

The zeolitic adsorbent of the invention preferably comprises macropores, mesopores as well as micropores. By «macropores», it is meant pores having an opening greater than 50 nm, preferably between 50 nm and 400 nm. By «mesopores», it is meant pores having an opening of between 2 nm and 50 nm, limits not included. By «micropores», it is mean pores having an opening smaller than 2 nm.

As previously indicated, the adsorbent of the present invention is in the form of an adsorbent having particle porosity of between 25% and 45%, preferably between 30% and 45%, more preferably between 32% and 45%, further preferably between 35% and 45%, and particularly advantageously between 36% and 45% limits included. Also, the standard deviation σ of crystal size distribution in said adsorbent is less than 0.30 μm, preferably between 0.05 μm and 0.30 μm, more preferably between 0.05 μm and 0.28 μm, further preferably between 0.10 μm and 0.28 μm, and most preferably between 0.10 μm and 0.25 μm, limits included.

The inventors have surprisingly discovered that when the standard deviation σ of crystal size distribution in the zeolitic adsorbent is greater than 0.30 μm, a drastic drop in productivity is observed in a para-xylene separation process, in particular in a liquid phase separation process in a simulated counter-current moving bed.

It was additionally surprisingly observed that this productivity value reaches a maximum with values of standard deviation σ of crystal size distribution in the zeolitic adsorbent agglomerate of less than 0.30 μm. This standard deviation σ value appears to correspond to optimized particle porosity. It was also observed in fully surprising manner that particle porosity is inversely proportional to the standard deviation σ of crystal size distribution in the zeolitic adsorbent agglomerate. Therefore, the more the standard deviation σ decreases, the more particle porosity increases. Yet, particle porosity that is too high leads to fully undesirable effects, such as loss of adsorption capacity for example, loss of mechanical strength, and others.

As a result, with the invention, persons skilled in the art desiring maximum productivity will find a trade-off between particle porosity and the standard deviation σ of crystal size distribution in the zeolitic adsorbent agglomerate. With the agglomerated adsorbent of the invention, it is thus possible to obtain maximum productivity in xylene separation processes.

Advantageously, the agglomerated zeolitic adsorbent is in the form of beads of mean diameter between 100 μm and 1000 μm, preferably between 100 μm and 600 μm, more preferably between 200 μm and 550 μm, limits included.

Preferably, the faujasite zeolitic adsorbent of the invention comprises barium and optionally potassium.

In a further embodiment of the invention, the zeolitic adsorbent has a content of barium expressed in barium oxide (BaO) higher than 10%, preferably higher than 15%, more preferably higher than 20%, further preferably higher than 23%, even higher than 33% by weight relative to the total weight of the adsorbent. Advantageously, the barium content is between 23% and 42%, and typically between 30% and 40% by weight, limits included, relative to the total weight of the adsorbent.

In another embodiment of the invention, the zeolitic adsorbent can have a content of potassium expressed in potassium oxide $K_2O$ lower than 25%, preferably between 0 and 20%, more preferably between 0 and 15% by weight, limits included, relative to the total weight of the adsorbent.

In another embodiment of the invention, the total content of alkali or alkaline-earth ions other than barium and potassium, expressed in oxides of alkali or alkaline-earth ions other than barium oxide BaO and potassium oxide $K_2O$ is between 0 and 5 weight %, limits included, relative to the total weight of the adsorbent.

Preferably, the zeolitic adsorbent of the present invention is an adsorbent containing FAU zeolite(s), generally referenced under the name zeolite of type X. By «zeolite X», it is meant a zeolite having a Si/Al atomic ratio of between 1.00 and 1.50 limits included, preferably between 1.00 and 1.40 limits included.

Among zeolites X, it is today commonly acknowledged that two sub-groups are recognised called zeolites LSX and zeolites MSX. Zeolites LSX have a Si/Al atomic ratio of about 1, i.e. 1.00±0.05, and zeolites MSX have a Si/Al atomic ratio of between about 1.05 and about 1.15, limits excluded.

In one preferred embodiment of the present invention, the zeolite X has a Si/Al atomic ratio of between 1.15 and 1.50, limits included. In another preferred embodiment, zeolite X is a zeolite of type LSX having a Si/Al atomic ratio of about 1, i.e. 1.00±0.05. It can also be envisaged that the adsorbent contains mixtures of two or more types of zeolite X such as just defined.

In one preferred embodiment, said at least one FAU zeolite included in the zeolitic adsorbent agglomerate of the invention has a Si/Al atomic ratio of between 1.00 and 1.50 limits included, preferably between 1.05 and 1.40 and more preferably between 1.10 and 1.40. Preferably, said at least one FAU zeolite is a zeolite X.

In another preferred embodiment, no zeolitic structure other than the FAU structure, preferably no zeolitic structure other than the faujasite X structure is detected by X-ray diffraction (known to skilled persons under the abbreviation XRD) in the zeolitic adsorbent agglomerate of the present invention.

In a further preferred embodiment, the weight fraction of FAU zeolite, the FAU zeolite preferably being a zeolite X, is higher than or equal to 80% relative to the total weight of the adsorbent of the present invention, the remainder up to 100% preferably being composed of non-zeolitic phase.

The zeolitic adsorbent agglomerates of the present invention can contain a non-zeolitic phase (NZP) i.e. a non-crystalline phase which is essentially inert against adsorption. The crystallinity content (weight fraction of zeolite) of the adsorbent of the invention can be measured by X-ray diffraction analysis known to skilled persons under the abbreviation XRD.

The zeolitic adsorbent agglomerate of the invention is preferably in the form of an agglomerate i.e. it is composed of crystalline elements (or crystals) of at least one FAU zeolite such as previously defined, said crystalline elements (or more simply «crystals») preferably having a number-weighted mean diameter of less than 1200 nm, preferably between 100 nm and 1200 nm, more preferably between 400 nm and 1200 nm, further preferably between 500 nm and 1200 nm, still further preferably between 550 nm and 1200 nm, and most advantageously between 600 nm and 1200 nm, limits included.

The zeolitic adsorbent agglomerates of the invention can be prepared by adapting operating modes already known to persons skilled in the art, as described for example in documents WO2014090771, WO2018002174, US2009/0326308 previously cited, and by selecting and adjusting the synthesis parameters allowing agglomerates to be obtained having the desired values of particle porosity and standard deviation σ.

A process for synthesizing the zeolitic adsorbent agglomerate of the present invention may, for example, comprise at least the steps of:

a) agglomerating crystals of at least one zeolite of FAU-X type with a binder comprising at least 80% of clay or mixture of zeolitizable clays, optionally with up to 5% of additives, and with an amount of water allowing the forming of the agglomerate material; drying the agglomerates at a temperature of between 50° C. and 150° C.; calcining the dried agglomerates under an oxidizing and/or inert purge gas in particular with gases such as oxygen, nitrogen, air, dry and/or decarbonated air, oxygen-depleted air optionally dry and/or decarbonated, at a temperature higher than 150° C., typically between 180° C. and 800° C., preferably between 200° C. and 650° C.;

b) zeolitizing all or part of the binder by contacting the agglomerates obtained at step a) with an alkaline base solution;

c) cationic exchange(s) of the agglomerates of step a) and/or step b) by contacting with a solution of barium ions and/or potassium ions;

d) optional, additional cationic exchange of the agglomerates of step c) by contacting with a solution of potassium ions;

e) washing and drying the agglomerates obtained at steps c) or d), at a temperature of between 50° C. and 150° C.; and f) activation by heating to a temperature generally of between 100° C. and 400° C., preferably between 200° C. and 300° C. followed by recovery of the zeolitic agglomerated adsorbent.

The zeolite crystals able to be used at synthesis step a) above can advantageously be synthesized following known operating modes available in the scientific literature or patent literature, and on the internet. In particular the zeolite crystals can be prepared as described in document CN1191118C, or WO2014090771, or U.S. Pat. No. 7,812, 208 B2, US2009326308 and US2007224113.

The parameters allowing control over the standard deviation σ in the zeolitic adsorbent agglomerate of the present invention are for example related to the type of crystals used at step a), in particular the size and standard deviation of said crystals, but also the zeolitization conditions of the agglomerating binder e.g. temperature, time, pH of the alkaline zeolitization solution, as well as duration, agitation mode, shear rate, pressure and others.

More specifically, by «type of crystals used at step a)», it is particularly meant the standard deviation of said crystals which can be controlled for example by adjusting the synthesis parameters and in particular synthesis temperature, agitation speed, shear rate as indicated for example in documents WO2009081022 or US2009326308.

The synthesis parameters allowing control over the porosity of the zeolitic adsorbent agglomerate of the invention are also known to skilled persons. In general, these parameters comprise but not limited thereto, the binder percentage, type of agglomeration (by extrusion, atomization, granulation, etc.), humidity level, type of binder, zeolitization conditions (temperature, time, pH of the alkaline zeolitization solution, duration, agitation mode, shear rate, pressure and others).

In one preferred embodiment, the synthesis of the zeolitic adsorbent agglomerate of the present invention does not comprise the addition of a pore-forming agent, the presence of a pore-forming agent possibly leading to degradation of crystallinity in particular.

It is also possible to prepare said crystalline elements by synthesis via seeding and/or adjustment of synthesis operation conditions such as $SiO_2/Al_2O_3$ ratio, sodium content and alkalinity of the synthesis mixture.

The synthesis of zeolite of FAU type is generally conducted in a sodium medium (Nat cation). The crystalline elements of FAU zeolite thus obtained mostly even exclusively contain sodium cations. It would remain within the scope of the invention however to use crystalline elements having undergone one or more cationic exchanges between synthesis in sodium form.

The size of the FAU zeolite crystals used at step a) and of the crystalline elements of FAU zeolite in the agglomerates of the invention is measured under scanning electron microscopy (SEM). As previously indicated, preferably the mean diameter of the crystals is generally less than 1200 nm, preferably between 100 nm and 1200 nm, more preferably between 400 nm and 1200 nm, further preferably between 500 nm and 1200 nm, still further preferably between 550 nm and 1200 nm, and most advantageously between 600 nm and 1200 nm, limits included.

This SEM observation also allows confirmation of the presence of a non-zeolitic phase, for example comprising residual binder (not converted at the zeolitization step) or any other amorphous phase in the agglomerates.

In the present document, the term «number-weighted mean diameter» is used or else «size», in particular for the crystalline zeolite elements and for the zeolitic adsorbents. The measuring method of these magnitudes is explained later in the description.

Agglomeration and forming (step a) can be performed using any technique known to skilled persons, such as extrusion, compacting, agglomeration on plate granulator, drum granulator, atomization and others.

The proportions of agglomerating binder (see definition below) and of zeolite used are typically those of the prior art i.e. 5 parts to 20 parts by weight of binder per 95 parts to 80 parts by weight of zeolite.

The agglomerates derived from step a), whether in the form of beads, extrudates or other, generally have a number-weighted mean diameter, or length (longest dimension when they are not spherical) of between 100 μm and 1000 μm, preferably between 100 μm and 600 μm, more preferably between 200 μm and 550 μm, limits included.

After step a), the finest agglomerates can be removed by cyclone removal and/or screening, and/or the agglomerates that are too large by screening or crushing in the case of extrudates for example.

The agglomerating binder used at step a) comprises and preferably consists of a clay or mixture of clays. These clays are preferably selected from among kaolins, kaolinites, nacrites, dickites, halloysites, attapulgites, sepiolites, montmorillonites, bentonites, illites and metakaolins, and the mixtures of two or more thereof in any proportion.

For the zeolitization step, the agglomerating binder used at step a) contains at least 80% preferably at least 90%, more preferably at least 95%, more particularly at least 96% by weight of at least one zeolitizable clay and may also contain other mineral binders such as bentonite, attapulgite, and others. By zeolitizable clay it is meant a clay or mixture of clays able to be converted to zeolitic material, most often through the action of an alkaline base solution. The zeolitizable clay generally belongs to the kaolin family (e.g. kaolinites, nacrites, dickites, halloysites) and/or metakaolins.

Among the additives optionally used at step a), these may include a silica source of any type known to skilled persons, specialists in the synthesis of zeolites, e.g. colloidal silica, diatoms, perlite, fly ash, sand, or any other form of solid silica.

At step a), in addition to the crystalline elements of FAU zeolite and binder, other additives can also be used e.g. additives intended to facilitate agglomeration or improve hardening, and other additives known to skilled persons.

In particular, if the agglomerating binder contains one or more zeolitizable clays, calcining allows the conversion of zeolitizable clay, typically kaolin, to meta-kaolin which can then be converted to zeolite at the zeolitization step (step b)). The principle thereof is set forth in «Zeolite Molecular Sieves» by D. W. Breck, John Wiley and Sons, New York, (1973), p. 314-315.

Zeolitization of the agglomerating binder is performed using any method currently well known to skilled persons, and for example can be performed by immersion of the product derived from step a) in an alkaline base solution, generally aqueous, for example an aqueous solution of sodium hydroxide and/or potassium hydroxide.

As a general rule, the concentration of the alkaline zeolitization solution is preferably between 0.5 M and 5 M. Zeolitization is preferably conducted under heat at a temperature higher than ambient temperature, and typically at temperatures in the region of 80° C. to 100° C. The duration of the zeolitization process is generally between a few tens of minutes and a few hours, preferably between about 1 hour and 8 hours.

Preferably, and to ensure full zeolitization of the binder without deteriorating the crystallinity of the zeolite crystals present, it is preferred to contact the adsorbents with a cold sodium hydroxide solution and to apply a gradual temperature rise up to a temperature of 80° C.-100° C.

Similarly, the concentration of sodium hydroxide can be maintained at the same concentration or it can be gradually increased to maintain maximum crystallinity of the initial crystals and to ensure maximum conversion of the zeolitizable binder.

The cationic exchange step(s) c) and d) are performed according to conventional methods known to skilled persons, and most often by contacting the agglomerates derived from step a) with a barium and/or potassium salt such as barium chloride ($BaCl_2$) and/or potassium chloride (KCl), in aqueous solution at a temperature of between ambient temperature and 100° C., preferably between 80° C. and 100° C. for rapid obtaining of high barium contents, expressed in barium oxide, i.e. preferably higher than 10%, more preferably higher than 15%, further preferably higher than 20%, still further preferably higher than 23%, even higher than 33% by weight relative to the total weight of the adsorbent.

Advantageously, the barium content, expressed in barium oxide, is between 23% and 42%, typically between 30% and 40% by weight, limits included, relative to the total weight of the adsorbent. It is preferred to operate with a large excess of barium ions relative to the zeolite cations it is desired to exchange, typically an excess in the region of 10 to 12, advantageously by proceeding via successive exchanges.

Optional exchange with potassium (step d) can be performed before and/or after exchange with barium (step c). As previously indicated, it is also possible at step a) to agglomerate crystalline elements of FAU zeolite already containing barium or potassium ions or barium and potassium (pre-exchange of the cations contained in the starting zeolite of FAU type, typically sodium cations, with barium or potassium ions or barium and potassium before step a) and to omit (or not omit) steps c) and/or d)).

After the cationic exchange step(s), washing is carried out generally and preferably with water followed by drying of the agglomerate thus obtained.

Activation which follows after drying is conducted in conventional manner using methods known to skilled persons e.g. at a temperature in general of between 100° C. and 400° C., preferably between 200° C. and 300° C. for a determined time as a function of desired water content and loss on ignition, typically from 1 hour to 6 hours.

Particle Size Measurement of the Zeolite Crystals:

Estimation of the number-weighted mean diameter of the elements (i.e. crystals) of FAU type zeolite used at step a) and of the elements (i.e. crystals) of zeolite X contained in the agglomerates is performed by observation under scanning electron microscopy (SEM).

To estimate the size of the particles (i.e. crystals) of zeolite on samples, a set of images is taken with magnification of at least 5000. The diameter is then measured of at least 200 particles using dedicated software e.g. Smile View software by LoGraMi. Accuracy is in the region of 3%. Measurement of the histogram formed from said diameter measurements allows the standard deviation σ of the distribution thereof to be determined at the same time.

Chemical Analysis of the Zeolitic Adsorbent Agglomerates—Si/Al Ratio and Rate of Exchange:

Elementary chemical analysis of the end product obtained after steps a) to f) described previously, can be carried out using different analytical techniques known to skilled persons. Among these techniques, mention can be made of X-ray fluorescence chemical analysis such as described in standard NF EN ISO 12677:2011 on a wavelength dispersive X-ray fluorescence spectrometer (WDXRF), e.g. Tiger S8 by Bruker.

X-ray fluorescence is a non-destructive spectral technique using the photoluminescence of atoms in the X-ray domain to determine the elementary composition of a sample. Excitation of the atoms, generally by an X-ray beam or electron bombardment, generates specific radiation after return to the fundamental state of the atom. The spectrum of X-ray fluorescence has the advantage of being very scarcely dependent on the chemical combination of the element, which affords precise determination both quantitative and qualitative. After calibration, the measurement uncertainty obtained for each oxide is conventionally less than 0.4 weight %.

These elementary chemical analyses allow verification of both the Si/Al atomic ratio of the zeolite used in the agglomerate and the Si/Al atomic ratio of the end product obtained after steps a) to f) previously described, as well as verification of the quality of the ionic exchange described at step c) and optional step d). In the description of the present invention, the measurement uncertainty of the Si/Al atomic ratio is ±5%.

Quality of ionic exchange is related to the number of moles of sodium oxide, $Na_2O$, remaining in the zeolitic agglomerate after exchange. More specifically, the rate of exchange by barium ions is estimated by evaluating the ratio between the number of moles of barium oxide BaO, and the number of moles of the group ($BaO+Na_2O$). Similarly, the rate of exchange by barium and/or potassium ions is estimated by evaluating the ratio between the number of moles of the barium oxide+potassium oxide total ($BaO+K_2O$) and the number of moles of the total ($BaO+K_2O+Na_2O$). It is to be noted that the contents of the different oxides are given in weight percentage relative to the total weight of the anhydrous zeolitic adsorbent.

Particle Size Measurement of the Zeolitic Adsorbents:

Determination of the number-weighted mean diameter of the zeolitic adsorbents obtained after the agglomeration and forming step a), is carried out by analysis of particle size distribution in a sample of agglomerate via imaging according to standard ISO 13322-2:2006, using a conveyor allowing the sample to pass in front of the camera.

The number-weighted mean diameter is then calculated from particle size distribution by applying standard ISO 9276-2:2001. In the present document, the term «number-weighted mean diameter» is used or else «size» for the zeolitic agglomerates. Accuracy is in the region of 0.01 mm for the size range of the agglomerates of the invention.

Mechanical Strength of the Zeolitic Adsorbents:

The crushing strength of a bed of zeolitic adsorbents such as described in the present invention is characterized by the Shell Method Series SMS1471-74 «Determination of Bulk Crushing Strength of Catalysts. Compression-Sieve Method», associated with «BCS Tester» apparatus marketed by Vinci Technologies. This method, initially intended for characterization of catalysts of 3 mm to 6 mm, is based on the use of a 425 μm screen allowing separation of the fines at the time of crushing. The use of a 425 μm screen remains suitable for particles of diameter greater than 1.6 mm, but must be adapted to the particle size of the agglomerates it is sought to characterize.

The agglomerates of the present invention, generally in the form of beads or extrudates, generally have a number-weighted mean diameter or length i.e. longest dimension for non-spherical agglomerates, of between 0.2 mm and 2 mm, and in particular between 0.2 mm and 0.8 mm, preferably between 0.4 mm and 0.65 mm, limits included. Consequently, a 100 μm screen is used instead of the 425 μm screen mentioned in Shell standard SMS1471-74.

The protocol for measurement is as follows: a 20 cm³ sample of agglomerated adsorbents, previously screened with the adapted screen (100 μm) and previously oven-dried for at least 2 hours at 250° C. (instead of 300° C. mentioned in Shell standard SMS1471-74), is placed in a metal cylinder of known internal cross-section. An increasing force is applied in incremental stages on this sample via a piston, through a 5 cm³ bed of stainless-steel beads for better distribution of the force applied by the piston on the adsorbent agglomerates (use of beads 2 mm in diameter for particles of spherical shape having a diameter of strictly less than 1.6 mm). The fines obtained at the different incremental stages of applied pressure are separated by screening (adapted 100 μm screen) and weighed.

In-bed crushing strength is determined by the pressure in megaPascals (MPa) at which the quantity of accumulated fines passing through the screen amount to 0.5 weight % of the sample. This value is obtained by plotting on a graph the mass of fines obtained as a function of the force applied to the bed of adsorbent and interpolating 0.5 weight % of accumulated fines. The in-bed crushing strength is typically between a few hundred kPa and a few tens of MPa and is generally between 0.3 MPa and 3.2 MPa. Accuracy is conventionally to within less than 0.1 MPa.

Non-Zeolitic Phase of the Zeolitic Adsorbents:

The percentage of non-zeolitic phase NZP, e.g. residual non-zeolitized binder or any other amorphous phase, after zeolitization, is calculated with the following equation:

$$NZP=100-\Sigma(ZP)$$

where ZP represents the sum of the quantities of zeolite X fractions in the meaning of the invention.

The percentage of zeolite X fractions (percent crystallinity) is measured by X-ray diffraction analysis known to skilled persons under the abbreviation XYD. This analysis is carried out on Bruker apparatus and the percentage of zeolite X fractions is evaluated with TOPAS software by Bruker.

Micropore Volume:

The crystallinity of the agglomerates is also evaluated by measuring the micropore volume thereof by comparing the latter with that of an appropriate reference (100% crystalline zeolite under same cationic treatment conditions, or theoretical zeolite). This micropore volume is determined from measurement of the gas adsorption isotherm, e.g. nitrogen, at the liquefying temperature thereof.

Prior to adsorption, the zeolitic adsorbent is degassed at between 300° C. and 450° C. for a time of between 9 hours and 16 hours, in a vacuum (P<6.7×10⁻⁴ Pa). Measurement of the nitrogen adsorption isotherm at 77 K is then performed on apparatus of type ASAP 2020 M by Micromeritics, taking at least 35 measurement points at relative pressures with a $P/P_0$ ratio of between 0.002 and 1.

Total Volume of Macropores and Mesopores, and Particle Porosity:

Macropore Vma and mesopore Vme volumes, particle density Dp and porosity $\varepsilon_p$ of macroporosity and mesoporosity type, are measured by mercury intrusion porosimetry. A mercury porosimeter of Autopore® 9500 type by Micromeritics is used to analyse the distribution of pore volume in the macropores and mesopores.

The experimental method described in the operating manual of the apparatus with reference to standard ASTM D4284-83, consists of placing a sample of adsorbent, (zeolitic adsorbent in agglomerate form to be measured) of known loss on ignition and previously weighed, in a porosimeter cell and after prior degassing (evacuation pressure of 30 μm mercury for at least 10 min), filling the cell with mercury at a given pressure (0.0036 MPa) and then applying increasing levels of pressure up to 400 MPa to cause the mercury gradually to enter the porous network of the sample, using at least 15 pressure levels up to 0.2 MPa, and then applying increments of 0.1 MPa up to 1 MPa, then 0.5 MPa up to 10 MPa, then 2 MPa up to 30 MPa, then 5 MPa up to 180 MPa, and finally 10 MPa up to 400 MPa.

The relationship between applied pressure and characteristic dimension of the pore entry threshold (corresponding to an apparent pore diameter) is determined using the Laplace-Young equation and assuming a cylindrical pore opening, a contact angle between mercury and the pore walls of 140° and mercury surface tension of 485 dynes cm⁻¹. The volume increments ΔVi of mercury inserted at each pressure level Pi are recorded, allowing subsequent plotting of the accumulated volume of inserted mercury as a function of applied pressure V(Pi), or as a function of the apparent diameter of the pores V(Ii). The value on and after which the mercury fills all inter-particle voids is set at 0.2 MP, and it is considered that above this value the mercury enters into the pores of the adsorbent. The particle volume Vp is then calculated by subtracting the accumulated volume of mercury at this pressure (0.2 MPa) from the volume of the porosimeter cell, and dividing this difference by the mass of equivalent anhydrous adsorbent i.e. the mass of said material corrected for loss on ignition. Particle density Dp is the inverse of particle volume Vp previously defined.

The macropore volume Vma of the adsorbent is defined as the accumulated volume of mercury inserted at a pressure of between 0.2 MPa and 30 MPa, corresponding to the volume contained in the pores of apparent diameter greater than 50 nm. The mesopore volume Vme of the adsorbent is defined as being the accumulated volume of mercury inserted at a pressure of between 30 MPa and 400 MPa. Since the method for measuring pore volume via mercury intrusion does not afford access to micropore volume, the total pore volume Vtot such as measured by mercury intrusion corresponds to the sum of the macropore Vma and mesopore Vme volumes.

In the present document, the macropore and mesopore volumes Vma and Vme, and the sum thereof (total pore volume Vtot), of the zeolitic adsorbents, expressed in cm³ g⁻¹, are therefore measured by mercury intrusion porosimetry and related to the mass of the sample in anhydrous equivalent i.e. the mass of said adsorbent corrected for loss on ignition. Particle density Dp is expressed in g cm⁻³ and refers to the mass of the sample in anhydrous equivalent.

Particle porosity $\varepsilon_p$ of macroporosity and mesoporosity type, is the product of particle density Dp multiplied by the sum of the macropore and mesopore volumes Vma and Vme:

$$\varepsilon p=Dp\times(Vma+Vme)$$

Loss on Ignition of the Zeolitic Adsorbents:

Loss on ignition is determined in an oxidizing atmosphere, by calcining the sample in air at a temperature of 900° C.±25° C., following the operating mode described in standard NF EN 196-2 (April 2006). The standard deviation of measurement is less than 0.1%.

EXAMPLES

Example 1: Preparation of the Agglomerates

Four adsorbents are prepared (Agglomerates 1, 3, 4, of the invention and a comparative Agglomerate 2) as described below, from a powder of faujasite zeolite of type X, the mean size of the crystals being 0.6 μm. The respective standard deviations of these crystals are 0.25 μm, 0.30 μm 0.35 μm and 0.50 μm.

Preparation of Agglomerate 1 (of the Invention)

A homogeneous mixture is prepared and 800 g of zeolite crystals of standard deviation 0.25 μm, are agglomerated with 160 g of kaolin (expressed in calcined equivalent) and 60 g of colloidal silica sold under the trade name Klebosol™ 30N50 (containing 30 weight % of $SiO_2$ and 0.5 weight % of $Na_2O$) with an amount of water allowing extrusion of the mixture. The extrudates are dried, calcined at 550° C. (firing of the clay) under a stream of nitrogen for 2 hours, and finally crushed to recover agglomerates having a number mean diameter of 0.5 mm.

The agglomerates obtained as described above (20 g) are placed in a double jacket glass reactor regulated at a temperature of 85° C.±1° C., to which are added 250 mL of 1M aqueous solution of sodium hydroxide and the reaction medium is left under agitation for a time of 5 hours.

The agglomerates are then washed with water in 3 successive wash operations and the reactor is drained. Efficacy of washing is checked by measuring the final pH of the wash waters, which is between 10.0 and 10.5.

The agglomerates are exchanged by contacting with 0.5 M solution of barium chloride at 95° C. in 4 steps. At each step, the ratio of solution volume to solid mass is 20 mL/g and exchange is continued for 4 hours each time. Between each exchange, the solid is washed several times to remove excess salt. The agglomerates are then dried at 80° C. for 2 hours and finally activated at 250° C. for 2 hours under a stream of nitrogen.

Preparation of Agglomerate 2 (Comparative)

A homogeneous mixture is prepared and 800 g of zeolite crystals, of standard deviation 0.50 μm, are agglomerated with 145 g of kaolin (expressed in calcined equivalent) and 55 g of colloidal silica sold under the trade name Klebosol™ 30N50 (containing 30 weight % of $SiO_2$ and 0.5 weight % of $Na_2O$) with an amount of water allowing extrusion of the mixture. The extrudates are dried, calcined at 550° C. (clay firing) under a stream of nitrogen for 2 hours, and finally crushed to recover agglomerates having a number mean diameter of 0.5 mm.

The agglomerates obtained as described above (20 g) are placed in a dual-jacketed glass reactor regulated at a temperature of 95° C.±1° C., to which are added 250 mL of 1.25 M aqueous solution of sodium hydroxide and the reaction medium is left under agitation for a time of 4 hours.

The agglomerates are then washed with water in 3 successive wash operations and the reactor is drained. Efficacy of washing is checked by measuring the final pH of the wash waters, which is between 10.0 and 10.5.

The agglomerates are exchanged by contacting with 0.5 M solution of barium chloride at 95° C. in 4 steps. At each step, the ratio of solution volume to solid mass is 20 mL g$^{-1}$ and the exchange is continued for 4 hours each time. Between each exchange, the solid is washed several times to remove excess salt. The agglomerates are then dried at 80° C. for 2 hours and finally activated at 250° C. for 2 hours under a stream of nitrogen.

Preparation of Agglomerate 3 (of the Invention)

A homogenous mixture is prepared and 800 g of zeolite crystals, of standard deviation 0.30 μm, are agglomerated with 160 g of kaolin (expressed in calcined equivalent) and 60 g of colloidal silica sold under the trade name Klebosol™ 30N50 (containing 30 weight % of $SiO_2$ and 0.5 weight % of $Na_2O$) with an amount of water allowing extrusion of the mixture. The extrudates are dried, calcined at 550° C. (clay firing) under a stream of nitrogen for 2 hours, and finally crushed to recover agglomerates having a number-weighted mean diameter of 0.5 mm.

The agglomerates obtained as described above (20 g) are placed in a dual-jacketed glass reactor regulated at a temperature of 90° C.±1° C., to which are added 250 mL of 0.9 M aqueous solution of sodium hydroxide and the reaction medium is left under agitation for a time of 6 hours.

The agglomerates are then washed with water in 3 successive wash operations and the reactor is drained. Efficacy of washing is checked by measuring the final pH of the wash waters, which is between 10.0 and 10.5.

The agglomerates are exchanged by contacting with 0.5 M solution of barium chloride at 95° C. in 4 steps. At each step, the ratio of solution volume to solid mass is 20 mL/g and exchange is continued for 4 hours each time. Between each exchange, the solid is washed several times to remove excess salt. The agglomerates are dried at 80° C. for 2 hours and finally activated at 250° C. for 2 hours under a stream of nitrogen.

Preparation of Agglomerate 4 (of the Invention)

A homogeneous mixture is prepared and 800 g of zeolite crystals, of standard deviation 0.35 μm, are agglomerated with 150 g of kaolin (expressed in calcined equivalent) and 58 g of colloidal silica sold under the trade name Klebosol™ 30N50 (containing 30 weight % of $SiO_2$ and 0.5 weight % of $Na_2O$) with an amount of water allowing extrusion of the mixture. The extrudates are dried, calcined at 550° C. (clay firing) under a stream of nitrogen for 2 hours, and finally crushed to recover agglomerates having a number-weighted mean diameter of 0.5 mm.

The agglomerates obtained as described above (20 g) are placed in a dual-jacketed glass reactor regulated at a temperature of 90° C.±1° C., to which are added 250 mL of 1.15 M aqueous solution of sodium hydroxide and the reaction medium is left under agitation for a time of 5 hours.

The agglomerates are then washed with water in 3 successive wash operations and the reactor is drained. Efficacy of washing is checked by measuring the final pH of the wash waters, which is between 10.0 and 10.5.

The agglomerates are exchanged by contacting with 0.5 M solution of barium chloride at 95° C. in 4 steps. At each step, the ratio of solution volume to solid mass is 20 mL/g and exchange is continued for 4 hours each time. Between each exchange, the solid is washed several times to remove excess salt. The agglomerates are then dried at 80° C. for 2 hours and finally activated at 250° C. for 2 hours under a stream of nitrogen.

Characteristics of Agglomerates 1 to 4

The mechanical strength (REL) of the agglomerates is characterized using the characterization techniques described above, and a value of 3.2 MPa is obtained for Agglomerate 1, a value of 3.1 MPa for Agglomerate 2, a value of 2.9 MPa for Agglomerate 3 and a value of 3.1 MPa for Agglomerate 4.

The values of particle porosity $\varepsilon_p$ and the standard deviations $\sigma$ of the crystals in the final agglomerates such as measured for Agglomerates 1 to 4 are given in Table 1 below.

Agglomerate 1 containing BaX crystals shows a mean crystal size measured on the final agglomerate of 0.79 μm, Agglomerate 2 containing BaX crystals shows a mean crystal size measured on the final agglomerate of 0.76 μm, Agglomerate 3 containing BaX crystals shows a mean crystal size measured on the final agglomerate of 0.77 μm, and Agglomerate 4 containing BaX crystals shows a mean crystal size measured on the final agglomerate of 0.76 μm.

The barium rates of exchange of Agglomerates 1 to 4, calculated from elementary analyses of barium and sodium oxides via X-ray fluorescence, as described in the characterization techniques, is 99.0%.

The BaO content in Agglomerates 1 to 4 is 36.2 weight %.

The loss on ignition measured as previously described is 5.2%±0.1%.

Example 2: Implementation in a Separation Process

Use of Agglomerates 1, 3 and 4

Agglomerates 1, 3 and 4 were used for the separation of paraxylene in a simulated moving bed.

The unit used, operating as simulated moving bed, was composed of 24 beds of length 1.1 m, with feed injection, desorbent injection, extract withdrawal and raffinate withdrawal. The beds were divided into 4 chromatographic zones with the configuration: 5/9/7/3.

The feed was composed of 50% para-xylene, 14.5% ortho-xylene, 30.6% meta-xylene and 4.9% ethylbenzene. The desorbent was para-diethylbenzene. The temperature was 175° C., and the pressure 15 bars. The water content was 95 ppm (weight).

The productivities obtained are given in Table 1 below. Superficial linear velocity in zone 3 was 1.63 cm s$^{-1}$.

Use of Agglomerate 2

Agglomerate 2 was used for the separation of paraxylene in a simulated moving bed.

The unit used, operating as simulated moving bed, was composed of 24 beds of length 1.1 m, with feed injection desorbent injection, extract withdrawal and raffinate withdrawal. The beds were divided into 4 chromatographic zones with the configuration: 5/9/7/3.

The feed was composed of 50% para-xylene, 14.5% ortho-xylene, 30.6% meta-xylene and 4.9% ethylbenzene. The desorbent was para-diethylbenzene. The temperature was 175° C., and pressure 15 bars. The water content was 95 ppm (weight).

Productivity was 186 kg of para-xylene m$^{-3}$ h$^{-1}$. Superficial linear velocity in zone 3 was 1.63 cm s$^{-1}$.

The productivity results of the four agglomerated adsorbents are given in Table 1 below.

TABLE 1

| | Particle porosity $\varepsilon_p$ (%) | Standard deviation $\sigma$ (μm) | Productivity (kg para-xylene m$^{-3}$ h$^{-1}$) |
| --- | --- | --- | --- |
| Agglomerate 1 (of the invention) | 35 | 0.21 | 220 |
| Agglomerate 2 (comparative) | 24 | 0.32 | 186 |
| Agglomerate 3 (of the invention) | 32 | 0.28 | 214 |

18

TABLE 1-continued

| | Particle porosity $\varepsilon_p$ (%) | Standard deviation $\sigma$ (μm) | Productivity (kg para-xylene m$^{-3}$ h$^{-1}$) |
| --- | --- | --- | --- |
| Agglomerate 4 (of the invention) | 38 | 0.15 | 223 |

It is clearly shown that the agglomerates of the invention allow a significant productivity gain to be obtained in the para-xylene production process.

The invention claimed is:

1. An agglomerated zeolitic adsorbent comprising at least one faujasite FAU-X zeolite of Si/Al atomic ratio between 1.00 and 1.50, limits included, and comprising barium and optionally potassium,
   wherein particle porosity of the absorbent is between 25% and 45%, limits included,
   wherein the standard deviation $\sigma$ of crystal size distribution in the agglomerate is between 0.05 and 0.30 μm, limits included, and
   wherein the adsorbent comprises zeolite crystals of number mean diameter less than 1200 nm.

2. The agglomerated zeolitic adsorbent according to claim 1, wherein the adsorbent comprises zeolite crystals of number mean diameter between 100 nm and 1200 nm.

3. The agglomerated zeolitic adsorbent according to claim 1, wherein the adsorbent is in the form of beads of mean diameter between 100 μm and 1000 μm, limits included.

4. The agglomerated zeolitic adsorbent according to claim 1, wherein the at least one FAU-X zeolite has a Si/Al atomic ratio of between 1.05 and 1.50, limits included.

5. The agglomerated zeolitic adsorbent according to claim 1, wherein the adsorbent comprises barium with a content of barium oxide (BaO) higher than 10%, relative to the total weight of the adsorbent.

6. The agglomerated zeolitic adsorbent according to claim 1, wherein the adsorbent comprises potassium with a content of potassium oxide K$_2$O lower than 25%, relative to the total weight of the adsorbent.

7. The agglomerated zeolitic adsorbent according to claim 1, wherein no zeolitic structure other than the faujasite structure is detected by X-ray diffraction.

8. The adsorbent according to claim 1 wherein the weight fraction of FAU zeolite is higher than or equal to 80% relative to the total weight of the adsorbent.

9. A process comprising separating para-xylene from aromatic isomer fractions having 8 carbon atoms, using as a para-xylene adsorption agent an agglomerated zeolitic adsorbent according to claim 1, in liquid phase or in gas phase.

10. The process comprising separating para-xylene from isomer fractions of aromatic hydrocarbons having 8 carbon atoms according to claim 9, in liquid phase further comprising adsorption of para-xylene in the presence of a desorbent.

11. The process according to claim 9 of simulated moving bed type.

12. The agglomerated zeolitic adsorbent according to claim 1, wherein the particle porosity of the absorbent is between 30% and 45%, limits included.

13. The agglomerated zeolitic adsorbent according to claim 1, wherein the particle porosity of the absorbent is between 36% and 45%, limits included.

14. The agglomerated zeolitic adsorbent according to claim 1, wherein the standard deviation σ of crystal size distribution in the agglomerate is between 0.1 μm and 0.28 μm, limits included.

15. The agglomerated zeolitic adsorbent according to claim 1, wherein the standard deviation σ of crystal size distribution in the agglomerate is between 0.1 μm and 0.25 μm, limits included.

16. The agglomerated zeolitic adsorbent according to claim 1, wherein the adsorbent comprises zeolite crystals of number mean diameter between 600 nm and 1200 nm.

17. The agglomerated zeolitic adsorbent according to claim 1, wherein the at least one FAU-X zeolite has a Si/Al atomic ratio of between 1.10 and 1.40, limits included.

18. The agglomerated zeolitic adsorbent according to claim 1 wherein the weight fraction of FAU-X zeolite is higher than or equal to 80% relative to the total weight of the adsorbent.

* * * * *